United States Patent [19]

Jacobsen et al.

[11] Patent Number: 5,248,295
[45] Date of Patent: Sep. 28, 1993

[54] BIOELECTRODE SEAL

[75] Inventors: Stephen C. Jacobsen; Tomasz J. Petelenz; Jon Beck; Robert L. Stephen, all of Salt Lake City, Utah

[73] Assignee: Iomed, Inc., Salt Lake City, Utah

[21] Appl. No.: 703,456

[22] Filed: May 21, 1991

Related U.S. Application Data

[63] Continuation of Ser. No. 348,596, May 8, 1989, abandoned.

[51] Int. Cl.$^5$ ............................................. A61N 1/30
[52] U.S. Cl. ........................................ 604/20; 607/148; 607/149
[58] Field of Search ............... 604/20; 128/798, 802, 128/803

[56] References Cited

U.S. PATENT DOCUMENTS

| | | | |
|---|---|---|---|
| 4,166,457 | 9/1979 | Jacobsen et al. | 128/803 |
| 4,419,092 | 12/1983 | Jacobsen et al. | 604/20 |
| 4,725,272 | 2/1988 | Gale | 424/448 |
| 4,784,857 | 11/1988 | Berry et al. | 424/449 |
| 4,810,582 | 3/1989 | Gould et al. | 424/449 |
| 4,838,273 | 6/1989 | Cartnell | 128/798 |
| 4,865,026 | 9/1989 | Barrett | 128/155 |
| 4,865,848 | 9/1989 | Cheng et al. | 424/449 |
| 4,895,169 | 1/1990 | Heath | 128/798 |
| 4,911,688 | 3/1990 | Jones | 604/20 |
| 4,911,916 | 3/1990 | Cleary | 424/449 |

*Primary Examiner*—Stephen C. Pellegrino
*Assistant Examiner*—Michael Rafa
*Attorney, Agent, or Firm*—Hana Dolezalova

[57] ABSTRACT

An iontophoretic bioelectrode includes an enclosure forming upper sheet of material having a generally planar outer section circumscribing a raised central section which defines an interior compartment. A compliant, resilient and sticky raised barrier is formed on the underside of the outer section of the upper sheet of material to circumscribe the central section. When placed against the skin of a person, the barrier adheres to the skin to form a seal completely around the central section and interior compartment into which an ion carrying solution may then be introduced for administration, by iontophoresis, into a persons' skin.

8 Claims, 1 Drawing Sheet

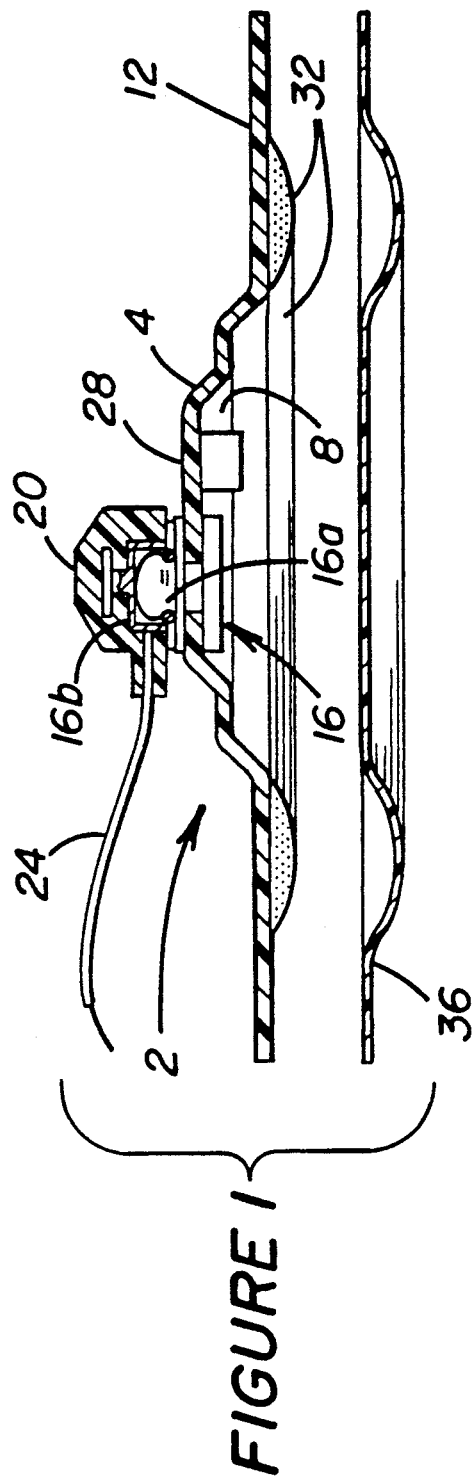
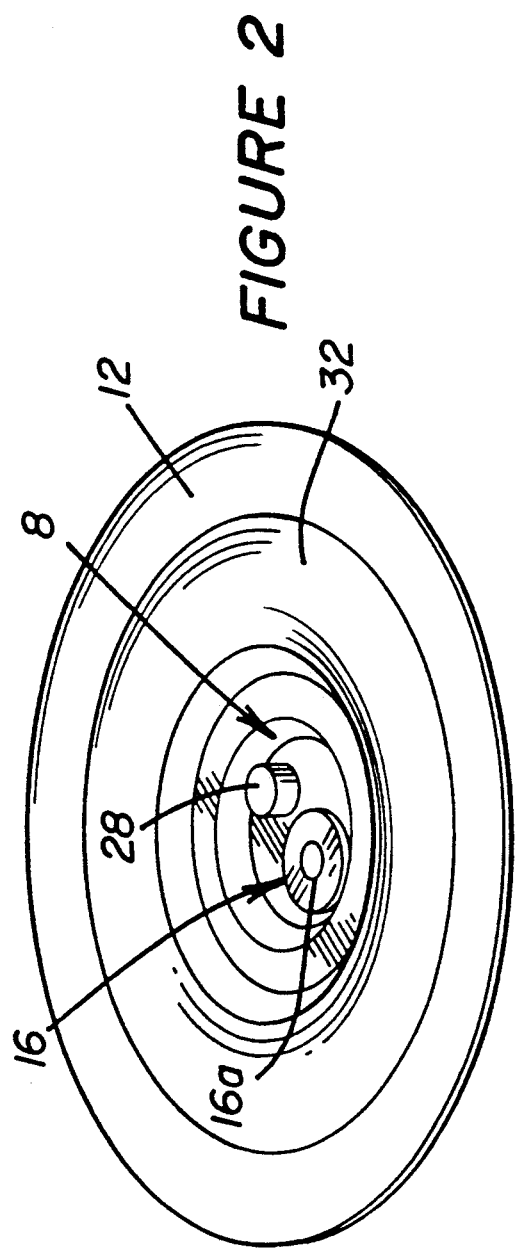

BIOELECTRODE SEAL

This is a continuation of application Ser. No. 07/348,596 filed May 8, 1989, abandoned.

BACKGROUND OF THE INVENTION

This invention relates to a new and improved iontophoretic bioelectrode structure incorporating a seal for preventing the leaking of solution when the bioelectrode is placed against a person's skin for use.

Iontophoresis is a technique of delivering ions into a person's skin or tissue by placing a solution or other medium containing the ions in contact with the skin, and applying electric current to the medium. The solution or medium containing the ions is typically carried by a first bioelectrode pouch or receptacle which, for administration of the medicament, is placed against the skin of a person so that the solution or medium is in contact with the skin surface. A second bioelectrode is placed against the person's skin in proximity to the first bioelectrode and electrical current of opposite polarity is applied to the second bioelectrode. In this manner, ions are caused to migrate from the ion carrying medium through the skin of the person. Sample patents where this technique is described are U.S. Pat. Nos. 4,141,359, 4,166,457, 4,419,092 and 4,477,971.

Prior to use, the bioelectrode is maintained and stored in a dry state (without the ion carrying solution). At the time of use, the bioelectrode is placed against the skin at the desired location, and then the solution is added or introduced into the bioelectrode. To accomplish this, structure is provided by which the ion carrying solution can be introduced by the user into the bioelectrode receptacle. Typically, a special structure is provided on the bioelectrode for receiving a solution applicator, and a special applicator structure is provided for supplying the solution to the bioelectrode. Such special structure is employed, among other things, to enable introduction of solution into the bioelectrode without puncturing it. One problem encountered with iontophoresis is that of leakage or spillage of the solution while the solution is being introduced into the bioelectrode receptacle, or while solution is being administered. This could occur, for example, if the bioelectrode is not securely placed against a person's skin so that gaps or openings between the skin and the bioelectrode exist. Then, when the solution was introduced to the bioelectrode receptacle, leakage could occur through these gaps.

One approach to minimizing the likelihood of leakage involves the use of a wettable barrier over the bioelectrode opening or, better yet, a microporous membrane. The membrane would be selected so as not to leak prior to use but yet to allow migration of ions therethrough to the skin upon application of an electric current to the ion carrying solution. The wettable barrier also serves to reduce the chance of leakage, although not as effectively as the microporous membrane. The disadvantage of both of these approaches, however, is the increased cost of providing either the wettable barrier or microporous membrane.

SUMMARY OF THE INVENTION

It is an object of the invention to provide a new and improved bioelectrode structure which is simple in design, easy and inexpensive to manufacture, and capable of substantially leak-free use.

It is another object of the invention to provide such a bioelectrode structure not requiring wettable barriers, microporous membranes, or other solution confining elements.

It is a further object of the invention to provide such a bioelectrode structure which facilitates attaching to the skin of a person to conform to skin surface irregularities and curves.

The above and other objects of the invention are realized in a bioelectrode structure which includes an enclosure forming upper sheet of material having a generally planar outer section circumscribing a raised central section which defines an interior compartment into which an ion carrying solution may be introduced. The bioelectrode structure also includes a compliant, resilient, flexible raised barrier formed on the underside of the outer section to circumscribe the central section for a conforming contact at a skin surface to thereby form a seal against the skin surface and prevent the leaking of solution from the interior compartment.

The bioelectrode structure of the present invention is used by placing the structure against the skin of a person and pressing the raised barrier against the skin to follow the contours thereof and form a tight annular seal about the central compartment of the bioelectrode.

Advantageously, the raised barrier is made of a material that is tacky or sticky to act as an adhesive as well as being compliant and resilient. Such tackiness facilitates maintaining the bioelectrode in place on a person's skin both while the solution is being introduced into the bioelectrode compartment and while the ions are being administered to the person's skin or tissue.

Also, the outer section of the bioelectrode advantageously is coated with an adhesive substance to facilitate a secure attachment of the outer section to the skin to thus hold the bioelectrode in place.

BRIEF DESCRIPTION OF THE DRAWINGS

The above and other objects, features and advantages of the invention will become apparent from a consideration of the following detailed description presented in connection with the accompanying drawings in which:

FIG. 1 is a side, cross-sectional view of a bioelectrode made in accordance with the principles of the present invention; and FIG. 2 is a perspective bottom view of the bioelectrode of FIG. 1.

DETAILED DESCRIPTION

Referring to FIG. 1, there is shown a bioelectrode composed of an upper sheet of material 2 having a raised or dome-shaped central section 4, defining an interior compartment or receptacle 8, and a generally planar outer section 12 which circumscribes the central section and is undercoated with an adhesive such as medical acrylate adhesive. The sheet of material 2 advantageously is made of plastic, polyvinyl chloride, polyurethane, or other material suitable for holding a solution. Attached to the sheet of material 2 to be exposed to the area under the sheet is a male element 16 of a conventional metallic snap used on clothing and the like. The element 16 includes a base portion 16a and an upper or nipple portion 16b projecting upwardly from the base portion. This structure is discussed in detail in U.S. Pat. Nos. 4,419,092 and 4,477,971.

A female element 20 is provided to fit over the nipple 16b as seen in FIG. 1. Disposed to extend between or through this element 20 to contact the nipple 16b when the element 20 is snapped thereover is a wire conductor 24. The conductor 24 leads to an electric current source not shown. Of course, other conventional methods of attaching a wire conductor to the element 16 could also be used.

Also attached to the underneath side of the upper sheet of material 2 is a receptacle structure (add-site) 28 through which ion containing solution is introduced into the bioelectrode. This structure consists of an annular conduit holding a plug at the upper end thereof through which a hypodermic needle may be inserted for introducing solution into the compartment 8 of the bioelectrode. An illustrative receptacle 28 is described in detail in the two aforecited U.S. Pat. Nos. 4,419,092 and 4,477,971.

Formed on and attached to the bottom surface of the outer section 12 of the upper sheet of material 2 is a compliant, resilient, hydrophobic and tacky or sticky raised barrier or ridge 32. This barrier 32 completely circumscribes the central section 4 and the compartment 8 formed by the central section in an annular fashion as best seen in FIG. 2.

The composition of the barrier 32 advantageously includes a silicon gel and silicon adhesive. Preferably, Dow Corning silicon gel Q7-2218 and Dow Corning silicon adhesive 355 is used, with four parts of Part A silicon gel, four parts of Part B silicon gel and three parts of adhesive being mixed, degassed thoroughly, dispensed into preformed molds, and cured for a period of time required for the particular mold material used. For example, for molds made of polystyrene, the curing time would be about eight hours at 65° C. After curing is completed, the upper sheet of a material 2 is overlayed on the barrier and attached to it by an adhesive. The resulting barrier 32 is compliant, resilient and sticky to allow adherence to the skin of a person. Because it is compliant, the barrier conforms to the skin surface shape to form the desired seal. Even though it is sticky, it may be readily removed from a person's skin without causing damage or discomfort.

The bioelectrode of the drawings is used by placing the electrode, bottom down, over the desired skin location to seal the compartment 8 from the outside. Then, after air is withdrawn from the compartment 8, a needle with ion carrying solution is inserted into the receptacle structure 22 and the solution is injected into the compartment. Electrical current may then be applied via conductor 24 to the metallic snap 16 and ultimately to the base portion 16A to commence the iontophoretic delivery of medication into the person's skin.

Referring again to FIG. 1, there is shown a protective cover 36 which is placed over the bottom of the bioelectrode to protect the parts thereof and especially the barrier 32 from damage or contamination. The cover 36 is simple plastic, coated with a release agent to allow easy removal from the barrier 32 prior to application of the bioelectrode to a person's skin. The stickiness of the barrier 32 (and also that of the outer section 12) is sufficient to hold the protective cover in place until time of use.

In the manner described, a simple and efficient bioelectrode is provided for the iontophoretic delivery of medication into the skin or tissue of a person. Provision of the compliant, resilient and sticky barrier 32 eliminates the need for a microporous membrane or other solution retaining structure being built into the electrode. The electrode may be put in place on a person's skin, the desired solution introduced into the electrode, and then the solution administered by iontophoresis into the person's skin in a simple and efficient fashion. The barrier 32 allows for sealing in the contents of the bioelectrode over contoured surfaces so that the bioelectrode may be applied to almost any location on the body.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A bioelectrode for delivery of an electrolyte solution into the skin or tissue, said bioelectrode comprising of the following components:
    an upper sheet of material suitable for holding a solution, said sheet having a raised central section for holding the electrolyte solution and a planar outer section circumscribing the central section, wherein a bottom surface of the planar outer section is undercoated with an adhesive material;
    a compliant, resilient, hydrophobic, and sticky seal forming a raised ridge, which seal is attached to the bottom surface of the planar outer section, and circumscribes the raised central section in an annular manner, wherein said seal conforms to the surface of the skin and allows its adherence to the skin; and
    a protective cover placed over the bottom of the bioelectrode for protection of the seal and of the raised central section wherein the stickness of the seal and the adhesive material of the planar outer section of the upper sheet are sufficient to hold the protective cover in place until time of use;
    wherein said upper sheet is made of plastic, polyvinyl chloride or polyurethane; and
    wherein the said seal is made of a combination of silicon gel and silicon adhesive material.

2. The bioelectrode according to claim 1 wherein said material is composed of eight parts of said silicon gel, and three parts of said silicon adhesive.

3. The bioelectrode according to claim 2 wherein said upper sheet is comprised of polyurethane.

4. The bioelectrode according to claim 3 wherein the adhesive material of the planar outer section of the upper sheet is medical acrylate adhesive.

5. The bioelectrode according to claim 4, wherein the protective cover place over the bottom of the bioelectrode is removably attached.

6. A compliant, resilient, and sticky seal useful as a sealing means in a bioelectrode for delivery of an electrolyte solution into the skin or tissue, wherein said seal is attached to and forms a raised ridge surrounding in an annular manner a bioelectrode receptacle for holding the electrolyte and allows adherence to the skin or tissue to seal the receptacle from the outside; wherein said seal is made of a combination of silicon gel and silicon adhesive material.

7. The seal according to claim 6 wherein the said material is composed of eight parts of silicon gel and three parts of silicon adhesive.

8. A seal made of compliant, resilient, hydrophobic, and sticky material wherein said material is prepared by steps:
    (a) mixing together eight parts of silicon gel and three parts of silicon adhesive;
    (b) degassing the mixture;
    (c) dispensing the degassed mixture into a mold; and
    (d) curing the mixture in the mold by heating said mixture at about 65° C. for about eight hours.

* * * * *